United States Patent
Chao Jung

(10) Patent No.: US 6,218,946 B1
(45) Date of Patent: Apr. 17, 2001

(54) BODY TEMPERATURE WARNING AND ALARMING DEVICE

(76) Inventor: Huang Chao Jung, No. 187, Lane 82, Jungjeng Rd., Daliau Shiang, Kaohsiung Shien (TW)

( * ) Notice: Subject to any disclaimer, the term of this patent is extended or adjusted under 35 U.S.C. 154(b) by 0 days.

(21) Appl. No.: 09/613,277

(22) Filed: Jul. 10, 2000

(51) Int. Cl.$^7$ .................................................. G08B 23/00
(52) U.S. Cl. ................ 340/573.1; 340/539; 340/870.17; 128/903; 374/141; 600/549
(58) Field of Search ................ 340/539, 573.1, 340/870.1; 600/549; 374/141; 128/903

(56) References Cited

U.S. PATENT DOCUMENTS

| | | | |
|---|---|---|---|
| 4,321,933 | * 3/1982 | Baessler | 600/549 |
| 4,471,354 | * 9/1984 | Smith | 340/870.17 |
| 4,819,860 | * 4/1989 | Hargrove et al. | 340/573.1 |
| 5,033,864 | * 7/1991 | Lasecki et al. | 600/549 |
| 5,581,238 | * 12/1996 | Change et al. | 340/573.1 |
| 5,938,619 | * 8/1999 | Dogre Cuevas | 600/549 |

* cited by examiner

Primary Examiner—Daniel J. Wu
(74) Attorney, Agent, or Firm—Dougherty & Troxell

(57) ABSTRACT

The present invention relates to a body temperature warning and alarming device comprising an emitter and a receiver. The emitter can be set at a displaying value or a warning and alarming value. A detected body temperature is emitted to the receiver to display a warning signal or to emit a warning signal, such that person wearing the receiver is informed, and a suitable or an appropriate treatment can be provided to the person wearing the emitter.

1 Claim, 3 Drawing Sheets

BODY TEMPERATURE WARNING AND ALARMING DEVICE

BACKGROUND OF THE INVENTION (a) Field of the Invention

The present invention relates to a body temperature warning and alarming device comprising an emitter and a receiver, wherein the emitter emits a detected temperature (from person wearing the emitter) to the receiver, and the temperature is displayed, and a waning or an alarming signal is thus produced so that the person wearing the receiver can proceed with suitable or appropriate treatment to the person wearing the emitter.

(b) Description of the Prior Art

It is important that the body temperature of a sick person be continuously observed. However, for a baby, it needs more intensive care to note the body temperature or temperature change when the baby is sick. It is not convenient to record the body temperature every hour as this is too tedious. Therefore, it is the aim of the inventor to design a warning and alarming device such that the body temperature of the person wearing an emitter is detected and emitted to the caretaker wearing a receiver. The caretaker is thus kept informed of temperature or temperature change of the baby or the patient. In this way, an appropriate treatment can be provided to the baby or the patient by the caretaker.

SUMMARY OF THE PRESENT INVENTION

Accordingly, an object of the present invention is to provide a body temperature waning and alarming device, wherein the emitter is set to emit a signal when a preset temperature warning valve and a temperature alarming value have reached The person wearing the receiver 2 is informed either by a sound signal or a vision signal with respect to the detected temperature emitted by the emitter.

Other objects, advantages, and novel features of the invention will become more apparent from the following detailed description when taken in conjunction with the accompanying drawings.

DETAILED DESCRIPTION OF THE PRESENT INVENTION

Figure 1:
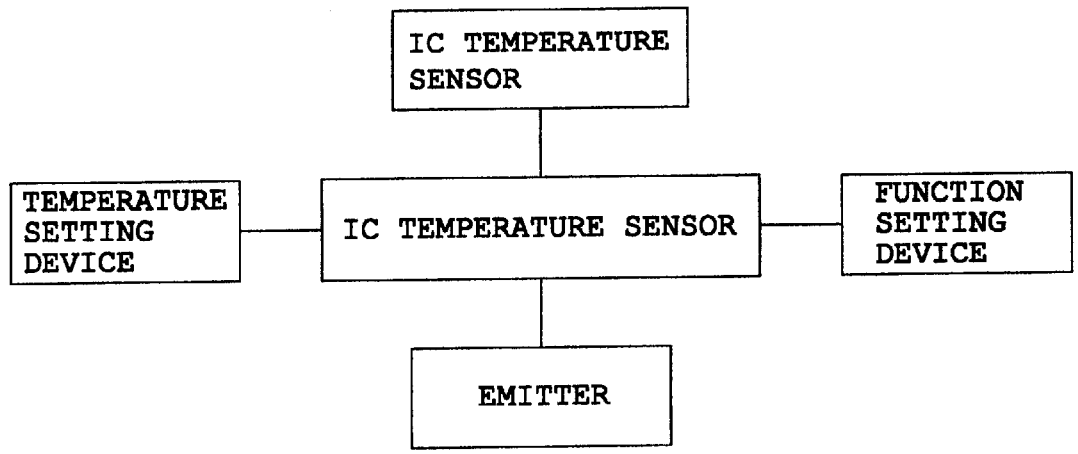
FIG. 1 is a block diagram of the emitter of the warning and alarming device of the present invention.
Figure 2:
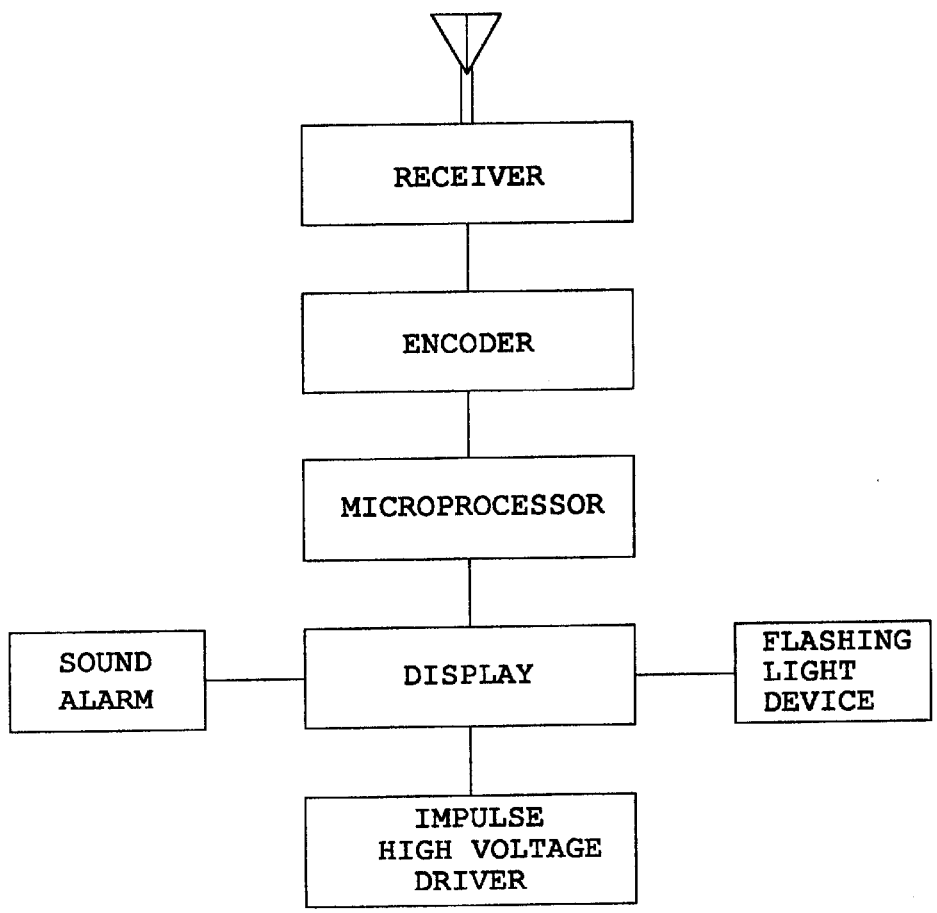
FIG. 2 is a block diagram of the receiver of the warning and alarming device of the present invention.
Figure 3:
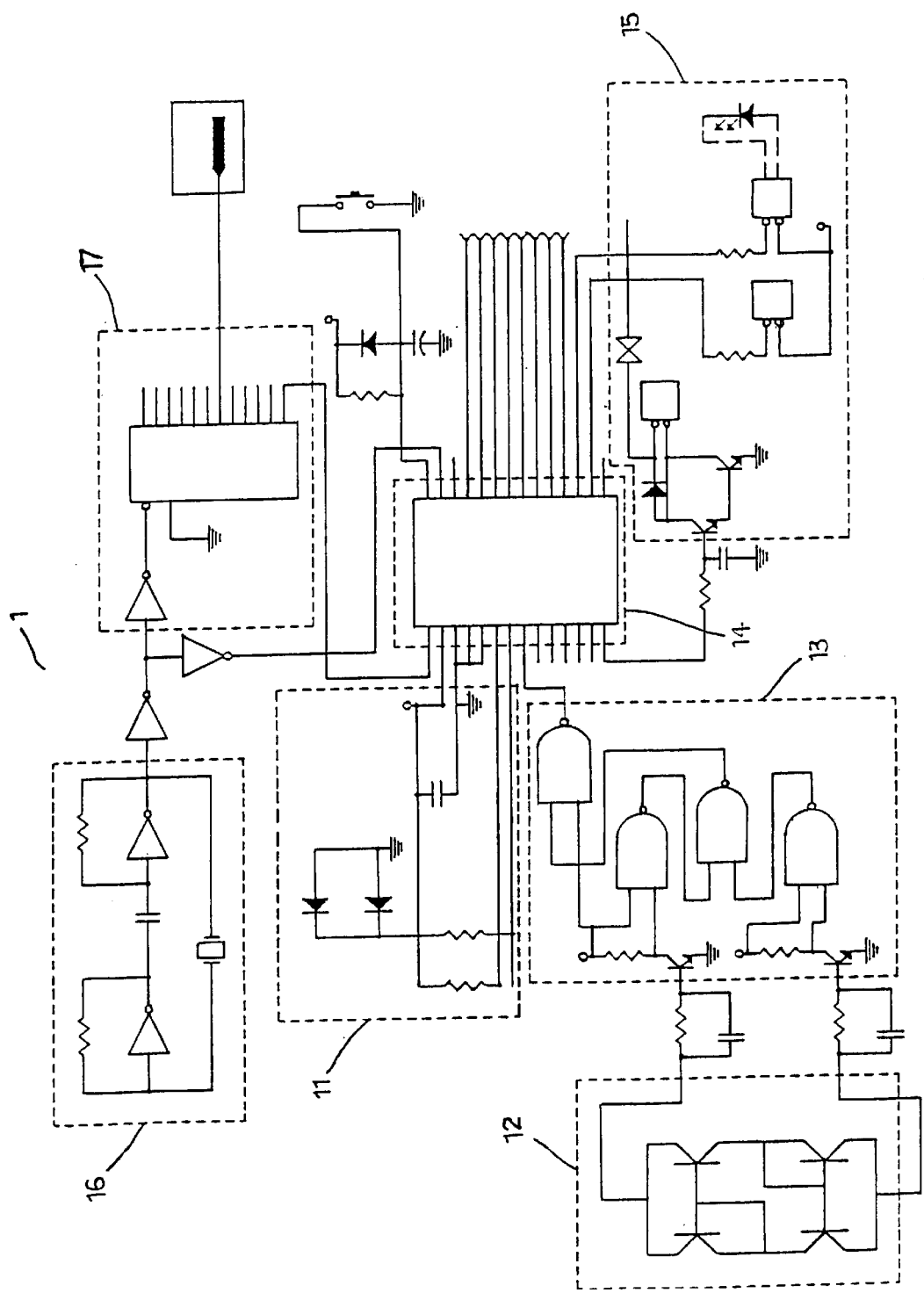
FIG. 3 is a circuit diagram of the emitter of the warning and alarming device of the present invention.
Figure 4:
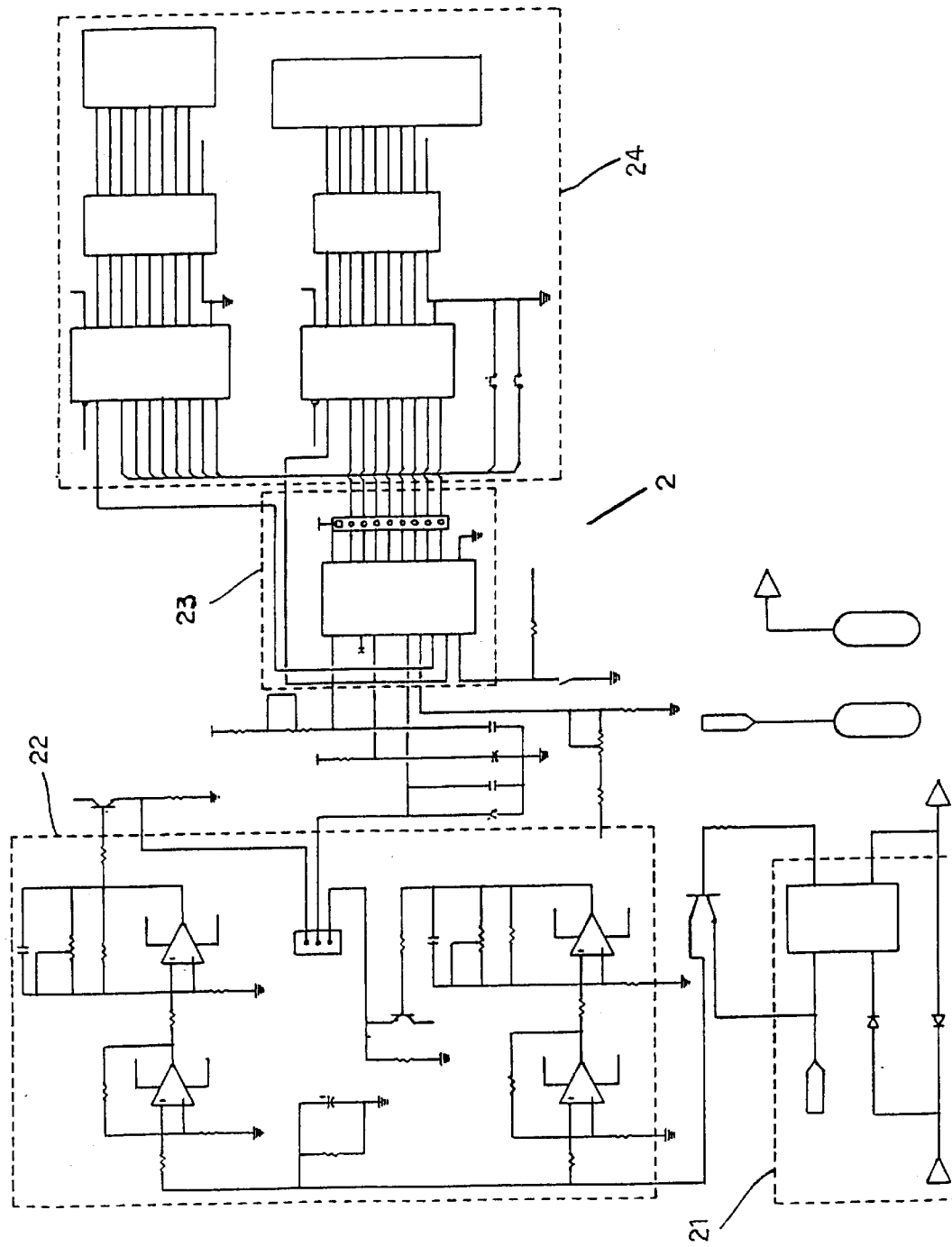
FIG. 4 is a circuit diagram of the receiver of the warning and alarming device of the present invention.

Referring to FIGS. 1 to 4, and in particular, to FIGS. 1 and 3, the body temperature warning and alarming device comprises an emitter 1 and a receiver 2, wherein the emitter 1 is mounted to the hand of a baby or a patient, and the receiver 2 is mounted to a person who is taking care of the baby or the patient The emitter 1 includes a power source circuit 11, a temperature sensor 12, a comparison circuit 13, a microprocessor 14, a function setting circuit 15, an oscillation circuit 16 and an emitting circuit 17. The temperature sensor 12 can detect the body temperature of the person wearing the emitter 1 and the temperature data detected by the temperature sensor 12 is transmitted to the comparison circuit 13 for processing, and then transmitted to the microprocessor 14 to convert the data signal into an indication. The function setting circuit 15 comprises three variable resistor modules 15a, 15b, 15c. The variable resistor module 15a is set such that one signal will be emitted to the receiver 2 for every increase of 0.1 to 5° C. In other words, a user can set the temperature increase by 0.1 or the temperature decrease by 1° C. in order to output a signal based on individual requirement. The variable resistor module 15b is set at a limiting value (for instance, at 38° C.) such that a warning signal is output to the receiver 2 so that the receiver 2 can emit a warning or a flash indication. The variable resistor module 15c is set to an alarming value (for instance, exceeding 38.5° C.) such that an alarming signal is transmitted to the receiver 2 to cause a production of an impulse high voltage. The person wearing the receiver 2 is shocked by the high voltage and reminded to pay attention to the temperature of the person wearing the emitter 1. The microprocessor 14 determines the signal from the comparison circuit 13 and that of the setting of the function setting circuit 15 to output a correct signal. The signal is amplified by the oscillation circuit 16 and then emitted by the emitting circuit 17.

The receiver 2 includes an aerial 21, a comparison circuit 23, a microprocessor 23 and a driving circuit 24, wherein, the emitted signal from the emitter 2 is received by the aerial 21 and read by the comparison circuit 22 to determine what kind of reaction is needed and then output the signal to the microcomputer 23. The microcomputer 23 determines the correct signal and then converts the signal to inform the driving circuit 24. The driving circuit 24 comprises a display module 24a and a warning module 24b, wherein, when the display module 24a has received the signal, the temperature is displayed on a monitor and the person wearing the receiver 2 can be informed of the temperature data by the monitor. When the warning module 24b has received the signal and the temperature has reached, a light flashing is produced to warn the person wearing the receiver 2. When the temperature is exceeded to the alarming value, then an impulse high voltage is produced and the person wearing the receiver 2 is provided with an electrical shock to awake him or remind him to take appropriate action or treatment. In accordance with the present invention, a 0.1 to 5° C. is set at the emitter 1 so that a warning indication is produced to the person wearing the receiver 2, and the body temperature of the person wearing the emitter 1 can be displayed without measuring the body temperature of the emitter 1 at a fixed period.

While this invention has been particularly shown and described with references to a preferred embodiment, it will be understood by those skilled in the art that various changes in form and details may be made therein without departing from the spirit and scope of the invention as defined by the appended claims.

I claim:

1. A body temperature warning and alarming device comprising an emitter and a receiver, wherein the emitter includes a power source circuit, a temperature sensor, a comparison circuit, a microprocessor, a function setting circuit, an oscillation circuit, and an emitting circuit, temperature data of person wearing the emitter is detected by the temperature sensor and is transmitted to the comparison circuit for processing, and then transmitted to the microprocessor to convert the data signal into indication, which is compared with a preset value made at the function setting circuit, the indication is amplified via the oscillation circuit and is then emitted by the emitter; wherein the receiver includes an aerial, a comparison circuit, a microprocessor and a driving circuit; the emitted signal from the emitter is received by the aerial and read by the comparison circuit to determine what kind of reaction is needed and then output the signal to the microcomputer; the microcomputer determines the correct signal and then convert the signal to inform the driving circuit to provide a displaying action or an alarming action, characterized in that the function setting circuit of the emitter comprises three variable resistor modules, wherein the first variable resistor module allows a temperature display within the range of 0.1 to 5° C.; the second variable resistor module provides setting of a warning value such that when the detected temperature reaches the warning value, the receiver emits a sound warning signal or a flash waning signal; and the third variable resistor module provides setting of an alarming value, thereby when the detected temperature has reached the alarming value, the receiver is driven to emit an impulse high voltage.

\* \* \* \* \*